United States Patent [19]

Matsuoka et al.

[11] 4,413,601
[45] Nov. 8, 1983

[54] METHOD FOR COMPUTING A COMPENSATION VALUE FOR AN ENGINE HAVING ELECTRONIC FUEL INJECTION CONTROL

[75] Inventors: Hiroki Matsuoka; Yukio Kinugasa, both of Susono; Takehisa Yaegashi, Mishima, all of Japan

[73] Assignee: Toyota Jidosha Kogyo Kabushiki Kaisha, Toyota, Japan

[21] Appl. No.: 326,074

[22] Filed: Nov. 30, 1981

[30] Foreign Application Priority Data

Jul. 9, 1981 [JP] Japan .................................. 56-106255

[51] Int. Cl.³ .......................... F02B 3/00; F02B 33/00
[52] U.S. Cl. .................................... 123/480; 123/486; 123/465; 123/440
[58] Field of Search ................ 123/480, 486, 465, 440

[56] References Cited

U.S. PATENT DOCUMENTS

| | | | |
|---|---|---|---|
| 4,130,095 | 12/1978 | Bowler | 123/480 |
| 4,201,161 | 5/1980 | Sasayama | 123/480 |
| 4,235,204 | 11/1980 | Rice | 123/480 |
| 4,306,529 | 12/1981 | Chiesa | 123/491 |
| 4,307,696 | 12/1981 | Noji | 123/465 |
| 4,309,971 | 1/1982 | Chiesa | 123/480 |

Primary Examiner—Ronald B. Cox
Attorney, Agent, or Firm—Cushman, Darby & Cushman

[57] ABSTRACT

A compensation value computing method for an electronic fuel injection controlled engine according to this invention measures an operating parameter for detecting the idling, low-load and high-load running conditions of the engine. First, second and third memory locations are provided corresponding, respectively, to these running conditions of the engine to compute feedback air-fuel ratios on the basis of feedback signals from an air-fuel ratio sensor. Values in the memory are compensated corresponding to the detected running conditions of the engine on the basis of the deviation of a feedback air-fuel ratio from the base air-fuel ratio. When the values in at least two memory locations differ from the base value by not less than a predetermined value, the altimetric compensation value is adjusted and when the difference between values in the first and third memories is larger than that between values in the second and third memories, the output compensation value of an air flow meter for detecting intake air flow is adjusted.

20 Claims, 8 Drawing Figures

METHOD FOR COMPUTING A COMPENSATION VALUE FOR AN ENGINE HAVING ELECTRONIC FUEL INJECTION CONTROL

This application is related to U.S. patent application Ser. No. 323,554, filed Nov. 20, 1981 which is assigned to the same assignee as the present invention.

BACKGROUND OF THE INVENTION

1. Field of the Invention

This invention relates to a method of and apparatus for an computing altimetric compensation value and an ouput compensation value of an air flow meter in an engine having electronic fuel injection control for operating a fuel injection valve according to electric signals to control the fuel supply to an intake system.

2. Description of the Prior Art

The density of air varies with the altitude in which an automobile travels. Also, the output characteristics of an air flow meter for detecting intake air flow are subjected to change over time since the intake air flow leaking from the periphery of a measuring plate swinging in relation to the intake air flow varies with the accumulation of strain on a wall of the air flow meter. Since the supply of fuel from a fuel injection valve in an engine with electronic fuel injection control is computed on the basis of the output of the air flow meter, it is necessary to compute a compensation value for the change in altitude or output characteristics of the air flow meter for compensating the fuel supply on the basis of this compensation value so as to maintain an air-fuel ratio of the mixture in a combustion chamber at a stoichiometric one. Also, in an engine wherein evaporated fuel adsorbed by activated charcoal as adsorbent is purged to the intake system during running of the engine to prevent the evaporated fuel from being purged from a fuel tank to the atmosphere, the air-fuel ratio of the mixture, i.e the output of air-fuel ratio sensor, varies with an amount of purged evaporated fuel in addition to the fuel supplied from the fuel injection valve. In the normal method of computing said compensation value, the feedback air-fuel ratio (the feedback air-fuel ratio represents the actual air-fuel ratio in the combustion chamber of the engine) is calculated on the basis of feedback signals from an air-fuel ratio sensor to adjust said compensation value on the basis of deviation of the feedback air-fuel ratio from the base one. However, when the running of the engine is once stopped and then resumed, it takes a predetermined time for the air-fuel ratio sensor to be properly heated to produce an effective output. Thus, for this predetermined time and during the low temperature of the engine, the feedback signal from the air-fuel ratio sensor is interrupted and an amount of fuel injection is calculated by an open loop control. Also, for this predetermined time and during the low temperature of the engine, the purging of the evaporated fuel to the intake system is interrupted and the amount of fuel injection, ignition timing, etc. is corrected on the basis of the final compensation value in the previous running of the engine so that the correction of the compensation value caused by the purging of the evaporated fuel to the intake system must be avoided.

In such a prior method of computing the compensation value, the running conditions of the engine are divided by the intake air flow into a plurality of ranges, for example, and a complementary RAM (Random Access Memory) is provided for each range. The data stored in the complementary RAM are always preserved in spite of the position of an ignition switch. The compensation values computed in every range on the basis of the deviation of the feedback air-fuel ratio from the base one are stored in a volatile RAM so that the number of the individual complementary RAMs is increased. Also in the prior computing method, the deviation of the feedback air-fuel ratio from the base one is limited in each range and when the deviation exceeds the limit, the compensation value is adjusted by the limit value, considering that the output of the air-fuel ratio sensor is affected by the purging of the evaporated fuel to the intake system. When an automobile travels from a low to a high altitude with high temperature and high speed (conditions in which a great amount of evaporated fuel is produced from a fuel tank), the deviation always exceeds the limit so that the change in the feedback air-fuel ratio caused by the change in the atmosphere is neglected and no altimetric compensation can be carried out by the prior method. Or, in another prior method of performing the altimetric compensation, a path of evaporated fuel purged to the intake system is closed by an electromagnetic valve to provide a purge interrupting period of the evaporated fuel for correcting the compensation value during this period. However, the accuracy of the air-fuel ratio is degraded since the frequency of correction of the compensation value during this period is reduced.

SUMMARY OF THE INVENTION

An object of this invention is to provide a method of and apparatus for computing a compensation value of an electric fuel injection controlled engine which can adjust an altimetric compensation value and output compensation value of an air flow meter with high accuracy and reduce substantially the number of individual complemetary memory elements.

In a method of computing a compensation value of an electronic fuel injection controlled engine according to this invention to accomplish this object, wherein a fuel injection valve is operated by electric signals to control the fuel supply to an intake system, an operating parameter is measured to detect the idling time, low-load time and high-load time of the engine and a first, second and third memory locations are provided, respectively, corresponding to these running conditions of the engine. A feedback air-fuel ratio is calculated on the basis of a feedback signal from an air-fuel ratio sensor. On the basis of deviation of the feedback air-fuel ratio from a base air-fuel ratio, the values in the memory locations are compensated corresponding to the detected running condition of the engine. When at least two values in two memory locations differ from the base value by more than a predetermined value, the altimetric compensation value is corrected. When the difference between the first memory value and the third one is more than that between the second one and the third one, the output compensation value of the air flow meter detecting intake air flow is corrected.

While the deviation of the feedback air-fuel ratio from the base air-fuel ratio, such as a stoichiometric one, changes with the purging of evaporated fuel to the intake system, changes in altitude and changes in the output characteristics of the air flow meter, the deviation caused by the purging of evaporated fuel to the intake system is zero during the idling time of the engine, is a maximum during low-load running and decreases during high-load running. Also, the deviation causes by the change in altitude is constant irrespective of the idling time, low-load time and high-load time, and the deviation caused by the change in the output characteristics of the air flow meter is large during the idling time and decreases as the load on the engine increases. Thus, when the deviation exceeding a predetermined value appears throughout the idling time, low-load time and high-load time of the engine, a change in altitude can be considered to have happened, and when the deviation increases in the order of high-load, low-load and idling times, the change in the output characteristics of the air flow meter can be considered to have happened. In such a case, the altimetric compensation and output compensation of the air flow meter can be carried out by correcting the altimetric compensation value and output compensation value of the air flow meter (hereinafter called "air flow meter compensation value"), respectively, according to this invention. Also, according to this invention, only the altimetric compensation value and air flow meter compensation value, are stored in the complementary memory elements, thereby eliminating the need to provide complementary memory elements for each of the many running ranges of the engine to store the compensation value of each running range in each complementary memory element, and the number of individual complementary memory elements can be substantially reduced. Further, according to this invention, the interruption of purging the evaporated fuel is not needed during the compensation period of the altimetric compensation value and air flow meter compensation value since the effect of the evaporated fuel on both compensation values is removed.

It is advantageous to detect the idling, low-load and high-load conditions of the engine on the basis of the intake airflow. These conditions may be detected on the basis of other parameters such as the intake pipe vacuum, rotational speed of the engine, opening of the throttle valve, etc, in addition to the intake air flow.

When an automobile moves from a high to a low altitude the engine may continue to travel without idling or travel only with low-load or idling of the engine without high-load. Thus, preferably the values in the first, second and third memory locations, provided respectively, corresponding to the idling, low-load and high-load times for storing values concerning the deviation of the feedback air-fuel ratio from the base one (hereinafter called "deviation data") are examined to correct the altimetric compensation value when the values in the first and second memory locations or the second and third memory locations are deviated from the base value towards the lean side of the mixture even if all the deviation data in the first to third memory locations are not deviated from the base value towards the side corresponding to the lean side of the mixture.

It is advantageous to limit the range of the altimetric compensation value and air flow meter compensation value for dealing with abnormalities such as the failure of the air-fuel ratio sensor, etc.

It is advantageous to correct the altimetric compensation value and air flow meter compensation value after the values in the first to third memory locations are compensated by a predetermined number of times for ensuring a predetermined reliability of these values.

The values in the first to the third memory locations, altimetric compensation value and air flow meter compensation value are corrected only when the temperature of the engine is within a predetermined range, for example, the temperature of the cooling water is 70°–90° C. and the output of the air-fuel ratio sensor is effective.

There also can be corrected when the amount of fuel injection is controlled by an open loop without the use of the detecting signal of the air-fuel ratio sensor.

DETAILED DESCRIPTION OF PREFERRED EMBODIMENTS

Figure 1:
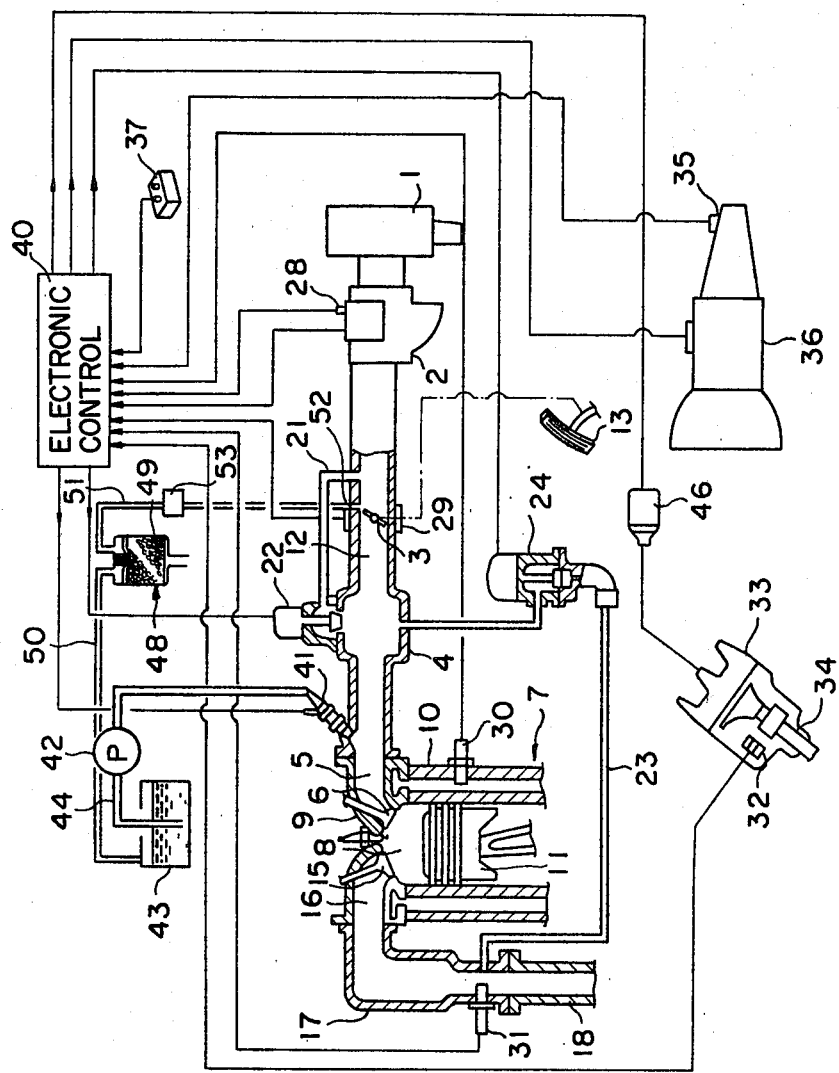
FIG. 1 is a system chart of an embodiment of an electronic fuel injection controlled engine according to this invention.

FIG. 1 is a system chart of an electronic fuel injection controlled engine according to this invention. Air sucked through an air cleaner 1 is sent to a combustion chamber 8 in an engine body 7 through an intake passage 12 including an air flow meter 2, throttle valve 3, surge-tank 4, intake port 5 and intake valve 6. The throttle valve 3 is interlocked with an accelerator pedal 13 in a cab. The combustion chamber 8 is defined by a cylinder head 9, cylinder block 10 and piston 11, and exhaust gas produced by the combustion of the mixture is purged to the atmosphere through an exhaust valve 15, exhaust port 16, exhaust manifold 17 and exhaust pipe 18. A bypass passage 21 interconnects the upstream side of the throttle valve 3 and the surge-tank 4, and a bypass flow controlling valve 22 controls the sectional flow area of the bypass passage 21 to maintain the rotational speed of the engine during the idling time at a constant speed. An exhaust gas recirculating (EGR) passage 23 guiding the exhaust gas to the intake system to restrain the production of nitric oxide interconnects the exhaust manifold 17 and the surge-tank 4, and an on/off valve type exhaust gas recirculating (EGR) controlling valve 24 opens and closes the EGR passage 23 in response to electric pulses. An intake temperature sensor 28 provided in the air flow meter 2 detects the temperature of the intake air and a throttle position sensor 29 detects the opening of the throttle valve 3. A water temperature sensor 30 mounted on the cylinder block 10 detects cooling water temperature, i.e. engine temperature, and an air-fuel ratio sensor 31, well-known as an oxygen concentration sensor, mounted on the aggregate of the exhaust manifold 17 detects the oxygen concentration in the aggregate. A crank angle sensor 32 detects the crank angle of a crankshaft (not shown) in the engine body 7 through the rotation of a shaft 34 of a distributer 33 connected to the crankshaft, and a vehicle speed sensor 35 detects the rotational speed of an output shaft of a transmission 36. The outputs of these sensors 2, 28, 29, 30, 31, 32, 35 and voltage of an accumulator 37 are input to an electronic control 40. A fuel injection valve 41 is provided near each intake port 5 corresponding to each cylinder, and a pump 42 sends fuel to the fuel injection valve 41 through a fuel passage 44 from a fuel tank 43. The electronic control 40 calculates the fuel injection amount on the basis of the parameters of the input signals from the respective sensors to send electric pulses having a pulse width corresponding to the calculated fuel injection amount to the fuel injection valve 41. Also, the electronic control 40 controls the bypass flow controlling valve 22, EGR controlling valve 24, a solenoid valve 45 (see FIG. 2) in an oil pressure controlling circuit of automatic transmission and a ignition coil 46. The secondary side of the ignition coil 46 is connected to the distributer 33. A charcoal canister 48 receives activated charcoal 49 as an adsorbent and has a port at the inlet side connected to the upper space of the fuel tank 43 through a path 50 and another port at the outlet side connected to a purge port 52 through a path 51. When the throttle valve 3 has an opening smaller than a predetermined one, the purge port 52 is located upstream of the throttle valve 3. On the other hand when the throttle valve 3 has an opening larger than the predetermined one, the purge port 52 is located downstream of the throttle valve 3 to be subjected to the intake pipe vacuum. A switch valve 53 having a bimetal disk closes the path 51 to stop the purging of evaporated fuel to the intake system when the engine has a low temperature lower than a predetermined one.

Figure 2:
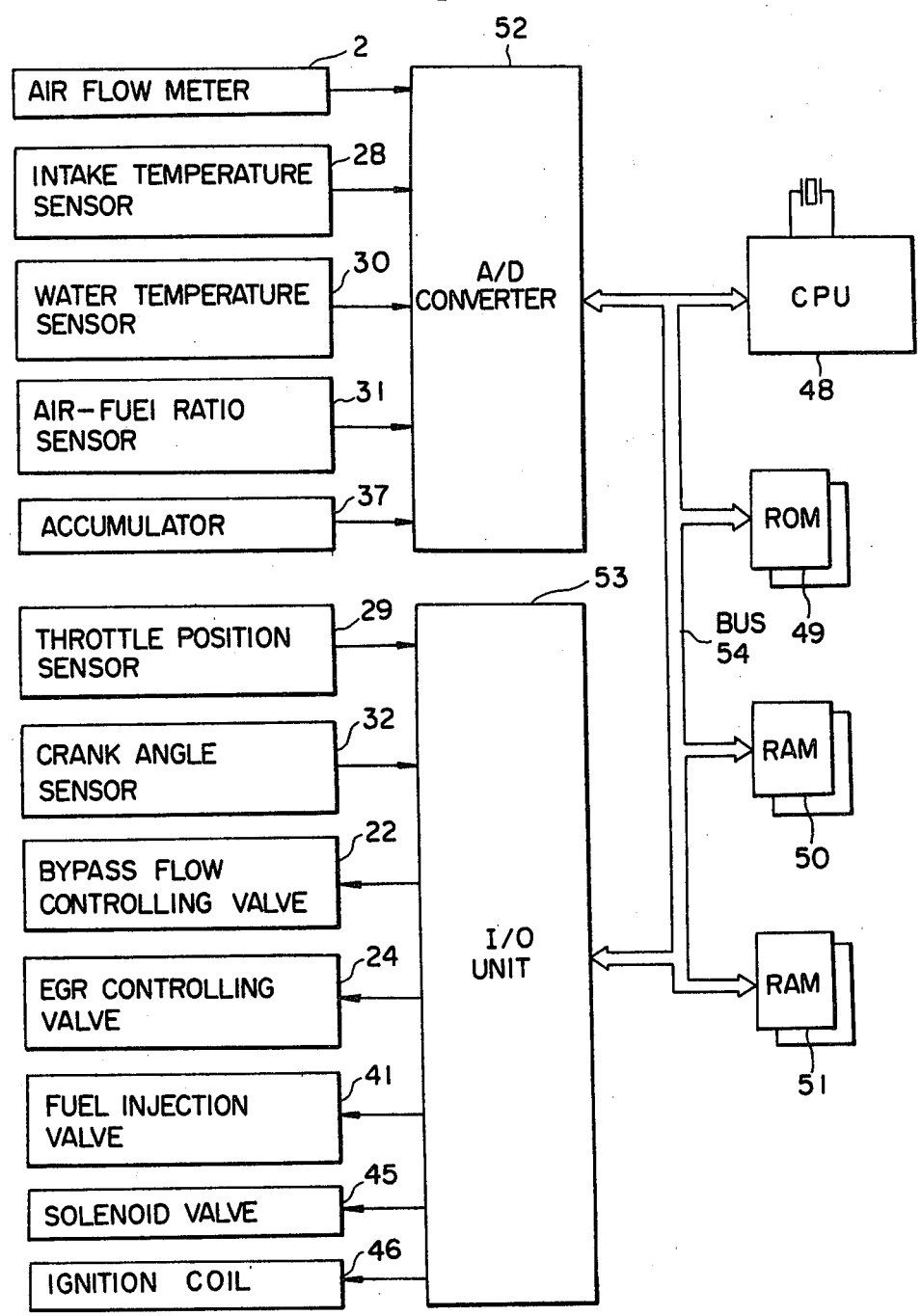
FIG. 2 is a block diagram of an electronic control shown in FIG. 1.

FIG. 2 shows details of the electronic control 40. A CPU (Central Process Unit) 48 consisting primarily of microprocessors a ROM (Read Only Memory) 49, a RAM (Random Access Memory) 50, another RAM 51 as a complementary memory element fed from an auxiliary power source even during the stoppage of the engine so as to be capable of retaining data, an A/D (Analogue/Digital) converter 52 with a multiplexer and an I/O (Input/Output) interface 53 with a buffer are connected to each other through a bus 54. The outputs of the air flow meter 2, intake temperature sensor 28, water temperature sensor 30, air-fuel ratio sensor 31 and accumulator 37 are input to the A/D converter 52. Also, the outputs of the throttle position sensor 29 and crank angle sensor 32 are input to the I/O interface 53, and the bypass flow controlling valve 22, EGR controlling valve 24, fuel injection valve 41, solenoid valve 45 and ignition coil 46 receive the output from the CPU 48 through the I/O interface 53.

Figure 3:
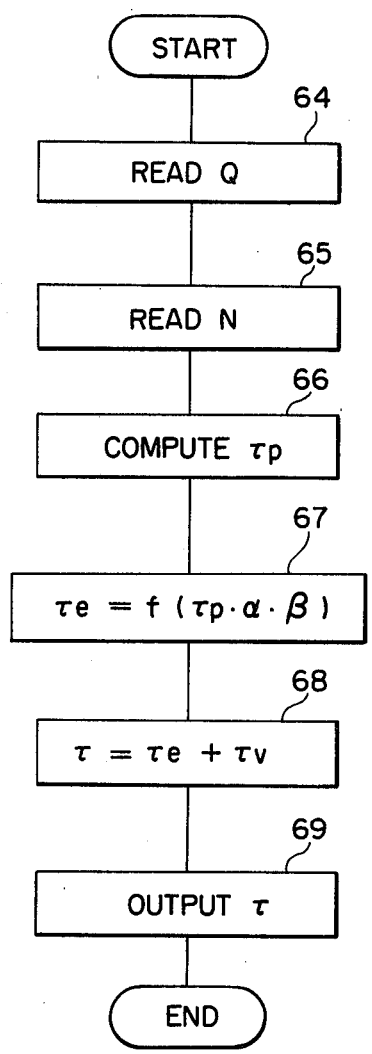
FIG. 3 is a flow chart of a program for calculating out fuel injection time.

FIG. 3 is a flow chart of a program for computing the fuel injection amount in the feedback control according to the parameter of the feedback signal from the air-fuel ratio sensor 31 when the engine temperature exceeds a predetermined value, i.e. after the completion of warming up the engine. Data concerning intake air flow Q and rotational speed N of the engine stored in the RAM 50 are read at steps 64, 65, and a basic injection time tp is obtained from these data at step 66. For the computation of $\tau p$ a prior well-known formula is used, for example, $\tau p = k \cdot Q/N$ (provided k is a constant). At step 67 is calculated $f(\tau p \cdot \alpha \cdot \beta)$ from a compensation factor $\alpha$ based on the feedback signal from the air-fuel ratio signal 31, a compensation factor $\beta$ based on the others (cooling water temperature, engine temperature, etc.) and $\tau p$ to provide an effective injection time $\tau e = f(\tau p \cdot \alpha \cdot \beta)$. At step 68 is calculated the final injection time $\tau = \tau e + \tau v$ from the effective injection time $\tau e$ and void injection time $\tau v$ of the fuel injection valve 41. At step 69 is sent $\tau$ is sent to the I/O interface 53.

Figure 4:
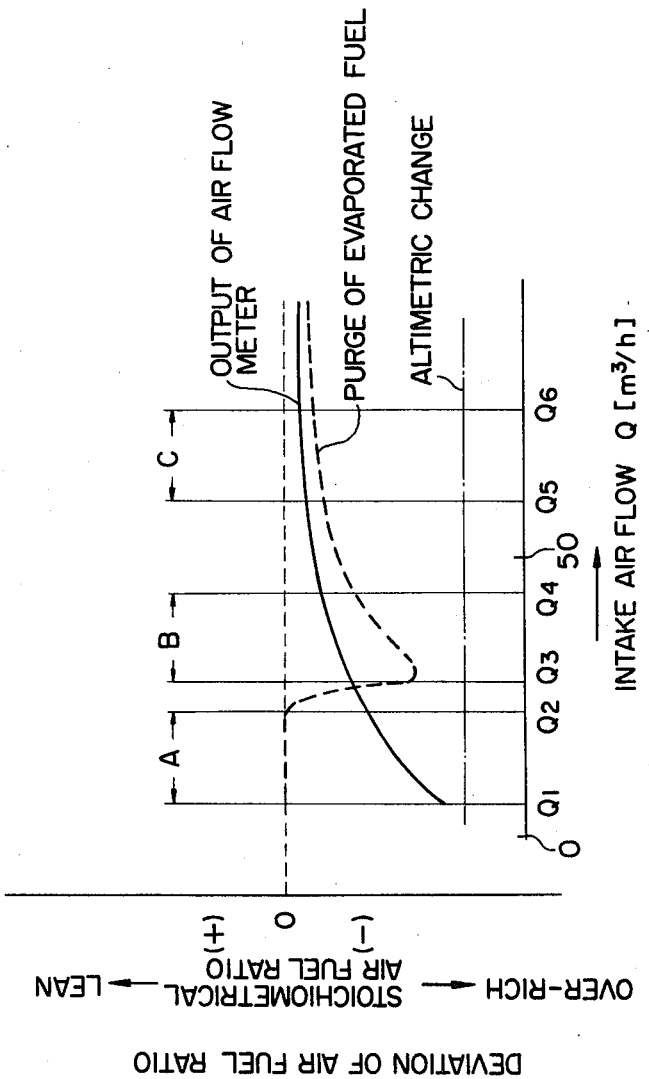
FIG. 4 is a graph showing the deviation of the air-fuel ratio caused by the output error of an air flow meter, etc.

FIG. 4 shows the relationship between the intake air flow and the deviation of the air-fuel ratio with respect to the output error (solid line) of the air flow meter 2, purging (broken line) of evaporated fuel to the intake system and altimetric change (dot-and-dash line). The stoichiometric air-fuel ratio as the base one corresponds to deviation=0. The relationship $Q1 < Q2 < Q3 < Q4 < Q5 < Q6$ is established and Q2 corresponds to the intake air flow when the throttle switch of the throttle position sensor 29 is reversed from on to off position. The throttle switch is turned on when the throttle valve 3 is in the idling opening, specifically the rotational angle of the throttle valve shaft is not more than 1.5°, and turned off when the throttle valve 3 has an opening larger than the idling opening. Q1 to Q6 are selected such that a first region A $(Q1 < Q < Q2)$, second region B $(Q3 < Q < Q4)$ and third region C $(Q5 < Q < Q6)$ correspond respectively to the idling, low-load and high-load times of the engine, and the first to third regions A, B and C are spaced from each other without overlapping with respect to the intake air flow Q. The deviation of the air-fuel ratio caused by the accumulation of strains on the inner wall of the air flow meter 2 increases as the intake air flow decreases. The deviation of the air-fuel ratio caused by the purging of evaporated fuel is zero in the first region A, the maximum in the second region B and decreases in the third region C. The deviation of the air-fuel ratio cuased by the altimetric change is constant irrespective of the intake air flow. The above is summarized as shown on the following table;

| Region | | A | B | C |
|---|---|---|---|---|
| Requirement | Idle switch | on | off | off |
| | Intake air flow | minimum | small | medium |
| Deviation due to output error of air flow meter | | large | medium | small |
| Deviation due to purge of evaporated fuel | | zero | large | small |
| Deviation due to altimetric change | | | constant | |

In FIG. 4, the deviation of the air-fuel ratio due to the altimetric change appears at the overrich side of the stoichiometric air-fuel ratio when an automobile moves from a low to a high altitude and the air density decreases. To the contrary, when the automobile moves from a high to a low altitude and the air density increases, the deviation of the air-fuel ratio appears at the lean side with respect to the stoichiometric air-fuel ratio. Assuming that the deviation at the stoichiometric air-fuel ratio is zero and the deviations at the lean and overrich sides are, respectively, plus and minus, the combined deviation of the air-fuel ratio as a result of these combined causes corresponds approximately to the combination of the characteristic lines shown in FIG. 4. Thus, from the above analysis of characteristics it is estimated that the deviation of the air-fuel ratio is caused by the altimetric change when the combined deviation exceeds a predetermined value in the three regions A, B, C. Also, when the difference between the combined deviation in the first region A and that in the third one C is larger than the difference between the combined deviation in the second region B and that in the third one C, the deviation of the air-fuel ratio can be estimated to be caused by the air flow meter.

Figure 5:
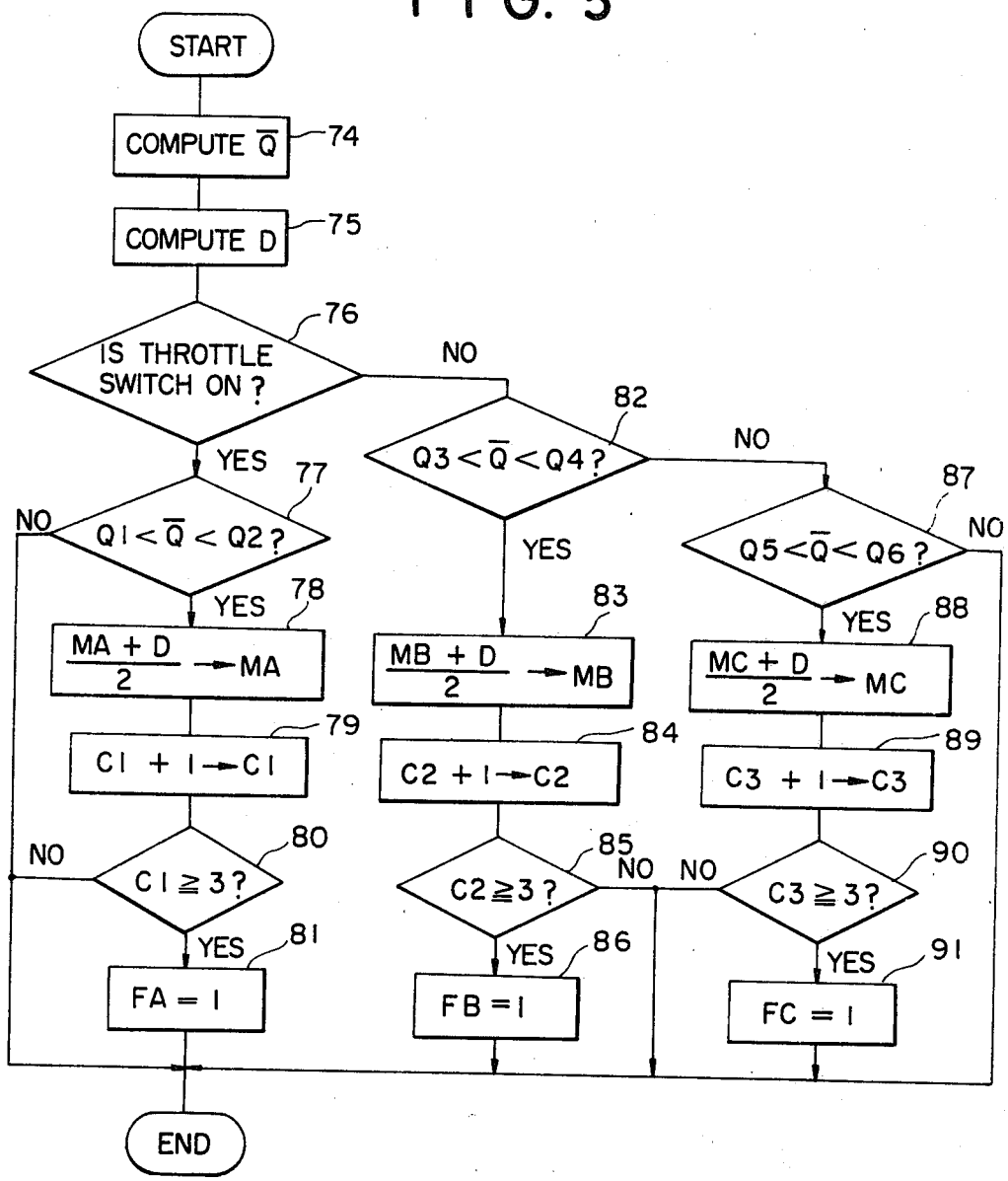
FIG. 5 is a flow chart of a program for calculating and storing deviation data.

FIG. 5 is a flow chart of a program for calculating and storing deviation data.

Figure 6:
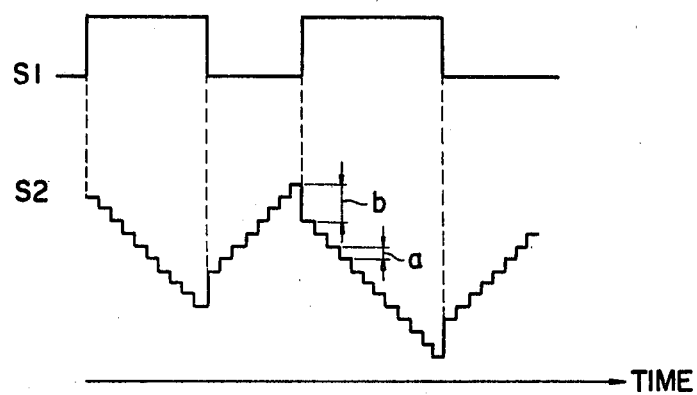
FIG. 6 exemplifies the relationship between the output of an air-fuel ratio sensor and the feedback air-fuel ratio.

At step 74, an average value Q of intake air flow per two cycles of air-fuel ratio feedback control is computed from detecting signals of the air flow meter 2. At step 75 is computed the deviation D of the average feedback air-fuel ratio from the stoichiometric air-fuel ratio in the same two cycles as those in the step 74. The unit of D is %, and the deviation D on the lean side with respect to the stoichiometric air-fuel ratio is plus, the deviation D on the overrich side being assumed minus. FIG. 6 exemplifies the feedback air-fuel ratio. $S_1$ is the output of the air-fuel ratio sensor 31 and $S_2$ the integrated value of the output of the air-fuel ratio sensor 31 as a feedback air-fuel ratio. Further, this integrated value is calculated by the CPU 48. The output of the air-fuel ratio sensor 31 is "1" when the air-fuel ratio is smaller than the stoichiometric air-fuel ratio, i.e. the mixture is overrich, and "0" when the air-fuel ratio is larger than the stoichiometric one, i.e. the mixture is lean. CPU 48 reduces the integrated value $S_2$ by a predetermined amount a at predetermined intervals while the output $S_1$ of the air-fuel ratio sensor 31 is maintained at "1", and increases the integrated value $S_2$ by the predetermined amount a at the predetermined intervals while the output $S_1$ of the air-fuel ratio sensor 31 is maintained at "0". Also, at the reversal of the output $S_1$ of the air-fuel ratio sensor 31, the integrated value $S_2$ is increased or decreased by another predetermined amount b where (b>a). The a and b vary with vehicle speed, b being set for improving the response. The integrated value $S_2$ corresponds to the actual air-fuel ratio of the mixture in the combustion chamber 8, i.e. the feedback air-fuel ratio.

At step 76 it is decided whether or not the throttle switch of the throttle position sensor 29 is turned on, and the process advances to step 77 if the switch is turned on, and to step 82 if it is not turned on. At step 77 it is decided whether or not $Q1<\overline{Q}<Q2$, i.e. the running condition of the engine is in the first region A, and the process advances to step 78 if the result of the decision is yes and terminates if it is no. At step 78, one-half of the sum of the values MA and D in the first memory M1 provided for the first region A is made a new value of MA where $(MA=D)/2\rightarrow MA)$. The value MA is cleared when the running of the engine is stopped or when step 130 (see FIG. 7), which will be described later, is carried out. $(MA+D)/2$ is made a new value of MA instead of making D a new value of MA as it is, since MA is prevented from being made an irrelevant value by any unexpected causes thereby improving the reliability of MA. At step 79 one is added to the value C1 of a first counter provided for the first region A. The value C1 of the first counter is cleared when the running of the engine is stopped or by the subsequent step 130. At step 80 it is decided whether the value C1 of the first counter is over three or not, and the process advances to step 81 if the result of the decision is yes and terminates if no. For example, even if D in the first time contains an error of 10%, the error of MA is reduced to 2.5% ($=10\%\div2\div2$) by the repetition of step 79 three times to improve the reliability of MA. At step 81 a first flag bit FA is set from 0 to 1. Flag bit FA=1 means that MA has been placed in a sufficiently reliable condition. At step 82 it is decided whether or not $Q3<\overline{Q}<Q4$, i.e. the running condition of the engine is in the second region B, and the process advances to step 83 is the result of the decision is yes and to step 87 if no. Steps 83, 84, 85 and 86 correspond to the above-mentioned steps 78, 79, 80 and 81. Namely, at step 83 one-half of the sum of the values MB and D in the second memory M2 provided for the second region B is made into a new value of MA where $((MB+D)/2\rightarrow MB)$. At step 84 one is added to the value C2 of a second counter provided for the second region B. At step 85 it is decided whether or not the value C2 of the second counter is at least three, and the process advances to step 86 if the result of the decision is yes and terminates if no. At step 86 a second flag bit FB is set from 0 to 1. At step 87 is decided whether or not $Q5<\overline{Q}<Q6$, i.e. the running condition of the engine is in the third region C, and the process advances to step 88 if the result of the decision is yes and terminates if not. Steps 88, 89, 90 and 91 correspond respectively to the above-mentioned steps 78, 79, 80 and 81. Namely, at step 88 one-half of the sum of the values MC and D in a third memory M3 provided for the third region C is made into a new value of MC where $((Mc+D)/2\rightarrow MC)$. At step 89 one is added to the value C3 of a third counter provided for the third region C. At step 90 it is decided whether the value C3 of the third counter is at least three or not, and the process advances to step 91 if the result of the decision is yes and terminates if not. At step 91 a third flag bit FC is set from 0 to 1.

Figure 7:
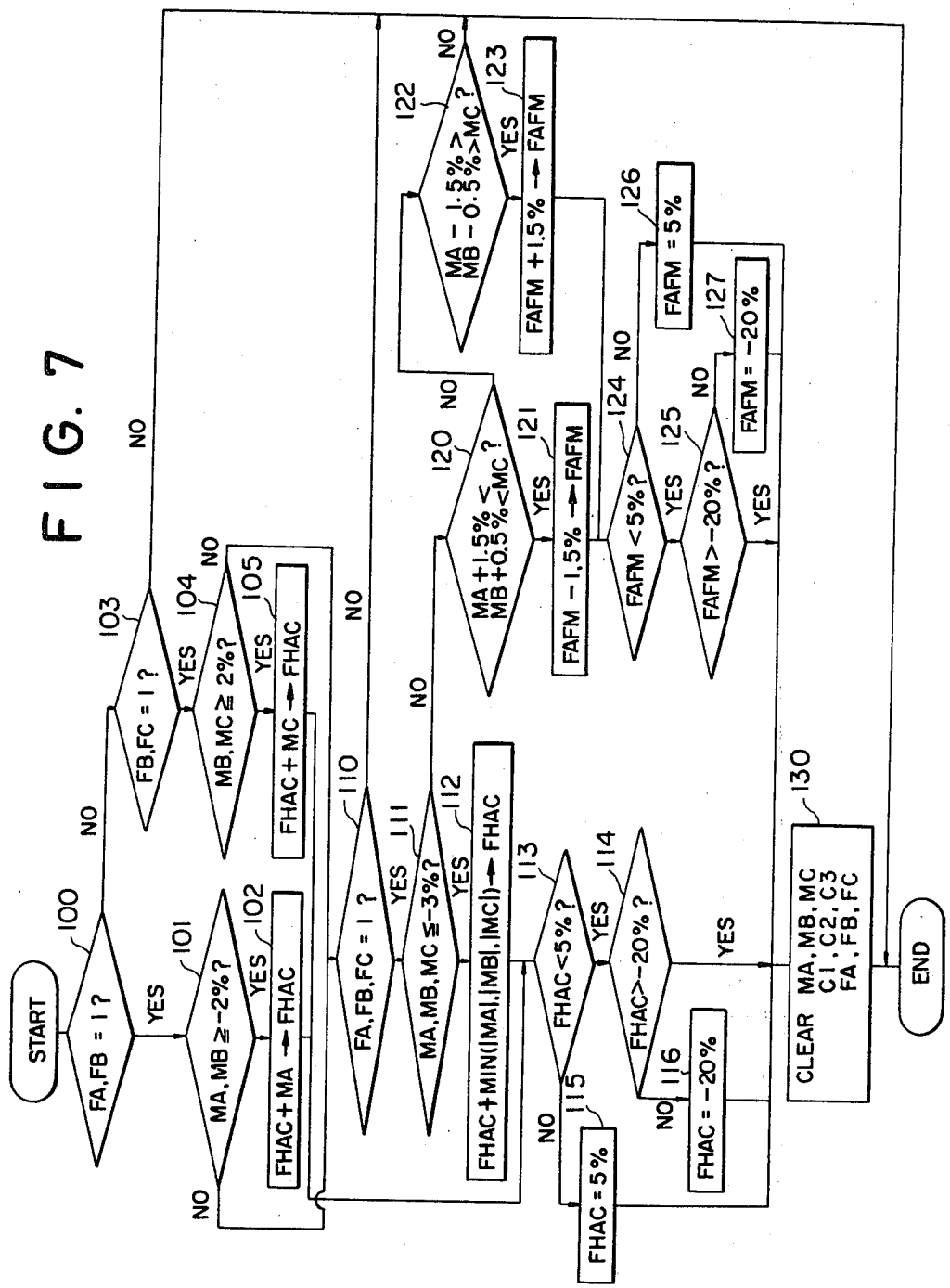
FIG. 7 is a flow chart of a program for calculating the altimetric compensation value and air flow meter compensation value.

FIG. 7 is a flow chart of a program for calculating the altimetric compensation value FHAC and air flow meter compensation value FAFM on the basis of the values in the first to third memory locations M1, M2 and M3, i.e. deviation data MA, MB and MC. At step 100 it is decided whether or not the flag bits FA, FB are both 1, and the process advances to step 101 if the result of the decision is yes and to step 103 if not. At step 101 it is decided whether or not the deviation data MA, MB are both at least 2%, i.e. deviated to the lean side by at least 2% with reference to the stoichiometric air-fuel ratio, and the process advance to step 102 if the result of the decision is yes and to step 110 if not. At step 102 is added the deviation data MA to the altimetric compensation value FHAC to make a new altimetric compensation value FHAC where $(FHAC+MA\rightarrow FHAC)$ and the process advances to step 113. At step 103 it is decided whether the flag bits FB, FC are both 1 and the process advances to step 104 if the result of the decision is yes and terminates if not. At step 104 it is decided whether or not the deviation data MB, MC are both at least 2% i.e. deviate by at least 2% to the lean side with reference to the stoichiometric air-fuel ratio, and the process advances to step 105 if the result of the decision is yes and to step 110 if not. At step 105 is added the deviation data MC to the altimetric compensation value FHAC where to make a new altimetric compensation value FHAC $(FHAC+MC\rightarrow FHAC)$ and the process advances to step 113.

When an automobile moves from a high to a low altitude as is apparent from the above analysis of FIG. 4, the feedback air-fuel ratio is deviated by at least a predetermined value to the lean side in the first, second and third regions A, B and C. However, some cases are expected where the engine is not run in the third region C, but only in the first and second regions A, B, i.e. the automobile travels down from the high to the low altitude without high load, or the engine is not run in the first region A but only in the second and third regions B, C, i.e. the automobile travels down from the high to the low altitude without stopping on the way. Accordingly when the deviation data MA, MB are both at least 2% or the deviation data MB, MC are both at least 2% like those in steps 101, 104, the altitude is considered lowered thereby requiring correction of the altimetric compensation value FHAC. For the correction of the altimetric compensation value FHAC in steps 102, 105 the deviation data MB is not used, but the deviation data MA or MC is used since the deviation data MA or MC is affected by the purging of evaporated fuel far less than the deviation data MB.

At step 110 it is decided whether or not any of the flag bits, FA, FB and FC is 1, and the process advances to step 111 if the result of the decision is yes and terminates if not. At step 111 it is decided whether or not any of the deviation data MA, MB and MC is not more than −3%, i.e. deviates by at least 3% to the overrich side with reference to the stoichiometric air-fuel ratio, the process advances to step 112 if the result of the decision is yes and to step 120 if not. At step 112 is added one of the deviation data MA, MB and MC closest to zero to the altimetric compensation value FHAC to make a new altimetric compensation value where (FHAC+min(≡MA≡, ≡MB≡, ≡MC≡)→FHAC). The deviation data closest to zero is selected since it has the minimum possibility of being affected by the purging of evaporated fuel than the others except for the altimetric change.

At step 113 it is decided whether or not the altimetric compensation value FHAC is less than 5%, and the process advances to step 114 if the result of the decision is yes and to step 115 if not. At step 114 it is decided whether or not the altimetric compensation value FHAC> −20%, and the process advances to step 130 if the result of the decision is yes and to step 116 if not. At step 115 the altimetric compensation value is set equal to FHAC 5%. At step 116 the altimetric compensation value FHAC is set equal to −20%. Steps 113 to 116 limit the range of the altimetric compensation value FHAC to prevent the altimetric compensation value FHAC from abnormal change due to unexpected causes like failure of the air-fuel ratio sensor 31 and others, and the upper limit (5%) is made smaller than the lower limit (−20%) with reference to the base value 0% since the altimetric compensation value FHAC for low altitude is selected for the base value.

At step 120 it is decided with reference to the deviation data MC whether or not the value (MA+1.5%) obtained from the sum of the deviation data MA and 1.5% is smaller than the value (MB+0.5%) obtained from the sum of the deviation data MB and 0.5% and the same value (MB+0.5%) is smaller than the deviation data MC and the process advances to step 121 if the result of the decision is yes and to step 122 if not. At step 121 is added −1.5% to the output compensation value FAFM of the air flow meter 2 to make a new compensation value FAFM. At step 122 it is decided with reference to the deviation data MC whether or not the value (MA−1.5%) obtained from the sum of the deviation data MA and −1.5% is larger than the value (MB−0.5%) obtained from the sum of the deviation data MB and −0.5% and the same value (MB−0.5%) is larger than the deviation data MC, and the process advances to step 123 if the result of the decision is yes and terminates if not. At step 123 is added 1.5% to the air flow meter compensation value FAFM.

In steps 120 to 123 it is decided whether or not characteristics as shown by the solid line in FIG. 4, i.e. characteristics that the more the intake air flow is reduced the farther the feedback air-fuel ratio is deviated from the base one, appear in the deviation data MA, MB and MC, and if they appear, 1.5% or −1.5% is added to the air flow meter compensation value FAFM to compensate it so that the feedback air fuel ratio approaches the stoichiometric one. The deviation of the air-fuel ratio due to the output error of the air flow meter 2 is the largest in the idling time and the deviation change of the air-fuel ratio due to the change in the air flow meter compensation value FAFM is small when the intake air flow is large, so that the air flow meter compensation value FAFM is compensated substantially by ±1.5% in alignment with the deviation in the idling time in steps 121, 123 so as to reduce the deviation in the idling time.

At step 124 it is decided whether or not the air flow meter compensation value FAFM is smaller than 5%, and the process advances to step 125 if the result of the decision is yes and to step 126 if not. At step 125 it is decided whether or not the compensation value FAFM is larger than −20%, and the process advances to step 130 if the result of the decision is yes and to step 127 if not. At step 126 the air flow meter compensation value FAFM is set equal to 5%. At step 127 is made the air flow meter compensation value FAFM −20%. Steps 124 to 127 limit the range of the air flow meter compensation value FAFM with the lower limit being larger than the upper limit since similar to the case of the altimetric compensation value FHAC, a new strainless air flow meter being assumed as a criterion.

At step 130 the first to third memory locations M1 to M3, the first to third counters and the first to third flag bits FA, FB and FC are cleared.

Since FHAC and FAFM are used during the open loop limit period until the output of the air-fuel ratio sensor 31 becomes effective when the engine is once stopped and then again run, they are stored in the complementary RAM 51.

The programs shown in FIGS. 5 and 7 are carried out when the engine temperature is in a predetermined range, i.e the temperature of the engine cooling water is, for example, between 70° C. and 90° C. and the output of the air-fuel ratio sensor 31 is effective. Also, these programs are carried out when the incremental compensation according to the water temperature is not carried out with reference to the base air-fuel ratio.

Figure 8:
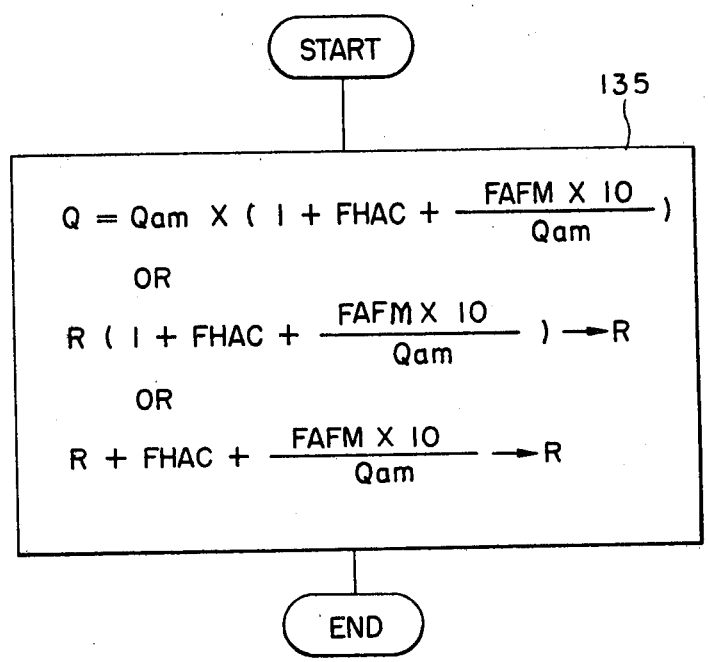
FIG. 8 is a flow chart of a program for correcting the intake air flow or base air-fuel ratio by the use of the altimetric compensation value and air flow meter compensation value.

FIG. 8 is a flow chart of a program for calculating the intake air flow Q or the base air-fuel ratio R. Assuming the intake air flow corresponding to the output of the air flow meter 2 is Qam, the intake air flow Q is calculated in step 135 from equation 1, where $Q = Qam \times (1 + FHAC + (FAFM \times 10)/Qam)$. In equation 1, FHAC and FAFM are not in %, but their decimal equivalents. The reason that FAFM is multiplied by 10 is because a representative intake air flow in the first region A is 10 cm³/h. The value of Q calculated from equation 1 is used for Q in step 64 in FIG. 3. The base air-fuel ratio is corrected in step 135 from the following equations;

$$R(1 + FHAC + (FAFM \times 10)/Qam) \rightarrow R \qquad (2)$$

$$R + FHAC + (FAFM \times 10)/Qam \rightarrow R \qquad (3)$$

The value of R is the quotient of the base air-fuel ratio divided by 14.8 (stoichiometric air-fuel ratio of gasoline at low altitude), and in equations 2 and 3 FHAC and FAFM are not in % but their decimal equivalents.

When the multiplication equation like equation 2 is used, accuracy is improved, and when the addition equation like equation 3 is used computational speed is improved. The value of R in the left side is the value before correction and can be considered a value corresponding to the stoichiometric air-fuel ratio in CPU 48, varying with the changes in altitude and in the output characteristics of the air flow meter 2. The value of R from equations 2 and 3 is reflected in the compensation factor $\alpha$ in step 67 of FIG. 3, and the value of Q in the program of FIG. 3 is equal to Qam when equations 2 and 3 are utilized.

What is claimed is:

1. A compensation value computing method for an electronic fuel injection controlled engine for controlling the fuel supply to an intake system by operating a fuel injection valve according to electric signals, said method comprising the steps of:

measuring an operating parameter of the engine;

detecting idling, low-load and high-load running conditions of the engine;

storing the measured operating parameter according to the detected running condition in one of first, second and third memory locations being provided corresponding, respectively, to said running conditions of the engine;

calculating a feedback air-fuel ratio on the basis of feedback signals from an air-fuel ratio sensor;

compensating the value in the memory location corresponding to the detected running condition of the engine on the basis of deviation of the feedback air-fuel ratio from a base air-fuel ratio;

adjusting an altimetric compensation value when values in at least two memory locations differ from a base value by not less than a predetermined value; and adjusting an output compensation value of an air flow meter for detecting intake air flow when the difference between values in the first and third memory locations are larger than that between values in the second and third memory locations.

2. A compensation value computing method for an electronic fuel injection controlled engine as defined in claim 1, including the step of storing the altimetric compensation value and output compensation value of the air flow meter in complementary memory elements.

3. A compensation value computing method for an electronic fuel injection controlled engine as defined in claim 2, wherein the step of detecting the idling, low-load and high-load running conditions of the engine are detected on the basis of the measured operating parameter, and wherein the step of measuring an operating parameter includes measuring the intake air flow.

4. A compensation value computing method for an electronic fuel injection controlled engine as defined in claim 3, wherein the step of adjusting the altimetric compensation value includes adjusting the altimetric compensation value on the basis of the value in the first memory location when the values in the first and second memory locations deviate to the side corresponding to the lean side of the mixture with reference to the base value.

5. A compensation value computing method for an electronic fuel injection controlled engine as defined in claim 3, wherein the step of adjusting the altimetric compensation value includes adjusting the altimetric compensation value on the basis of one of the values in the first to third memory locations which is the closest to the base value when any of the values in the first, second and third memory locations deviate to the side corresponding to the overrich side of the mixture with reference to the base value.

6. A compensation value computing method for an electronic fuel injection controlled engine as defined in claim 3, including the step of limiting the range of the altimetric compensation value and output compensation value of the air flow meter.

7. A compensation value computing method for an electronic fuel injection controlled engine as defined in claim 3, wherein the steps of adjusting the altimetric compensation value and output compensation value of the air flow meter are executed after the step of compensating the values in the first to third memory locations is repeated a predetermined number of times.

8. A compensation value computing method for an electronic fuel injection controlled engine as defined in claim 3, including the steps of measuring the engine temperature and determining if it is within a predetermined range before the steps of compensating the values in the first to third memory locations based upon the deviation of the feedback air-fuel ratio from the base air-fuel ratio and adjusting the altimetric compensation value and output compensation value of the air flow meter.

9. A compensation value computing method for an electronic fuel injection controlled engine as defined in claim 3, including the steps of measuring the water temperature of the engine and applying incremental compensation based on the water temperature to the base air-fuel ratio and inhibiting the steps of compensating the values in the first to third memory locations based upon the deviation of the feedback air-fuel ratio from the base air-fuel ratio and the adjustment of the altimetric compensation value and output compensation value of the air flow meter.

10. A compensation value computing method for an electronic fuel injection controlled engine as defined in claim 3, wherein the step of adjusting the altimetric compensation value includes adjusting the altimetric compensation value on the basis of the value in the third memory location when the values in the second and third memory locations deviate to the side corresponding to the lean side of the mixture with reference to the base value.

11. A compensation value computing apparatus for an electronic fuel injection controlled engine for controlling the fuel supply to an intake system by operating a fuel injection valve according to electric signals, said apparatus comprising:

means for measuring an operating parameter of the engine;

an air-fuel ratio sensor for producing feedback signals;

a memory having first, second and third memory locations; and process means for, determining the idling, low-load and high-load running conditions of the engine;

storing the measured operating parameter according to the detected running condition in one of the first, second and third memory locations being provided corresponding, respectively, to said running conditions of the engine;

calculating a feedback air-fuel ratio on the basis of the feedback signals from the air-fuel ratio sensor;

comparing the feedback air-fuel ratio to a base air-fuel ratio;

compensating the value in the memory location corresponding to the detected running condition of the engine on the basis of the deviation of the feedback air-fuel ratio from the base air-fuel ratio;

adjusting an altimetric compensation value when values in at least two memory locations differ from a base value by not less than a predetermined value; and adjusting an output compensation value of the means for measuring the operating parameter when the differnece between values in the first and third memory locations is larger than that between values in the second and third memory locations.

12. A compensation value computing apparatus for an electronic fuel injection controlled engine as defined in claim 11, including complementary memory elements for storing the altimetric compensation value and output compensation value of the means for measuring the operating parameter.

13. A compensation value computing apparatus for an electronic fuel injection controlled engine as defined in claim 12, wherein the means for measuring an operating parameter includes an air flow meter for measuring the intake air flow, and wherein the idling, low-load and high-load running conditions of the engine are determined on the basis of the intake air flow.

14. A compensation value computing apparatus for an electronic fuel injection controlled engine as defined in claim 13, wherein the altimetric compensation value is adjusted on the basis of the value in the first memory location when the values in the first and second memory locations deviate to the side corresponding to the lean side of the mixture with reference to the base value.

15. A compensation value computing apparatus for an electronic fuel injection controlled engine as defined in claim 13, wherein the altimetric compensation value is adjusted on the basis of one of the values in the first to third memory locations which is the closest to the base value when any of the values in the first, second and third memory locations deviate to the side corresponding to the overrich side of the mixture with reference to the base value.

16. A compensation value computing apparatus for an electronic fuel injection controlled engine as defined in claim 13, wherein the processing means limits the range of the altimetric compensation value and output compensation value of the means for measuring the operating parameter.

17. A compensation value computing apparatus for an electronic fuel injection controlled engine as defined in claim 13, wherein the processing means compensates the values in the first to third memory locations a predetermined number of times before the altimetric compensation value and output compensation value of the means for measuring the operating parameter are adjusted.

18. A compensation value computing apparatus for an electronic fuel injection controlled engine as defined in claim 13, including means for measuring the engine temperature, and wherein the processing means determines if it is within a predetermined range before compensating the values in the first to third memory locations based upon the deviation of the feedback air-fuel ratio from the base air-fuel ratio and the adjustment of the altimetric compensation value and output compensation value of the means for measuring the operating parameter.

19. A compensation value computing apparatus for an electronic fuel injection controlled engine as defined in claim 13, including means for measuring the water temperature of the engine, and wherein the processing means incrementally compensates the base air-fuel ratio based on the water temperature and inhibits the compensation of the values in the first to third memory locations based upon the deviation of the feedback air-fuel ratio from the base air-fuel ratio and the adjustment of the altimetric compensation value and output compensation value of the means for measuring the operating parameter.

20. A compensation value computing apparatus for an electronic fuel injection controlled engine as defined in claim 13, wherein the altimetric compensation value is adjusted on the basis of the value in the third memory location when the values in the second and third memory locations deviate to the side corresponding to the lean side of the mixture with reference to the base value.

* * * * *